United States Patent
Kinoshita et al.

(10) Patent No.: US 8,076,679 B2
(45) Date of Patent: Dec. 13, 2011

(54) NITRIDE-BASED SEMICONDUCTOR LIGHT-EMITTING DIODE AND ILLUMINATING DEVICE

(75) Inventors: Yoshitaka Kinoshita, Kagoshima (JP); Hidenori Kamei, Fukuoka (JP)

(73) Assignee: Panasonic Corporation, Osaka (JP)

(*) Notice: Subject to any disclaimer, the term of this patent is extended or adjusted under 35 U.S.C. 154(b) by 200 days.

(21) Appl. No.: 10/593,446

(22) PCT Filed: Mar. 18, 2005

(86) PCT No.: PCT/JP2005/005003
§ 371 (c)(1),
(2), (4) Date: Sep. 19, 2006

(87) PCT Pub. No.: WO2005/091385
PCT Pub. Date: Sep. 29, 2005

(65) Prior Publication Data
US 2007/0284588 A1    Dec. 13, 2007

(30) Foreign Application Priority Data
Mar. 19, 2004    (JP) .................................. 2004-079873

(51) Int. Cl.
*H01L 33/00*    (2010.01)
(52) U.S. Cl. ... 257/88; 257/213; 257/256; 257/E33.065; 257/E33.068
(58) Field of Classification Search .................... 257/88, 257/213, 256, 257, E33.065, E33.068
See application file for complete search history.

(56) References Cited

U.S. PATENT DOCUMENTS

| | | | |
|---|---|---|---|
| 5,656,832 A | 8/1997 | Ohba et al. | |
| 5,793,054 A * | 8/1998 | Nido | 257/18 |
| 5,909,040 A | 6/1999 | Ohba et al. | |
| 5,929,466 A | 7/1999 | Ohba et al. | |
| 6,172,382 B1 | 1/2001 | Nagahama et al. | |
| 6,340,824 B1 | 1/2002 | Komoto et al. | |
| 2001/0048064 A1* | 12/2001 | Kitani | 250/208.1 |
| 2002/0079506 A1 | 6/2002 | Komoto et al. | |
| 2002/0088985 A1 | 7/2002 | Komoto et al. | |
| 2002/0179923 A1 | 12/2002 | Morita et al. | |
| 2003/0022028 A1 | 1/2003 | Koike et al. | |

(Continued)

FOREIGN PATENT DOCUMENTS
JP    11-214798    8/1999
(Continued)

OTHER PUBLICATIONS

Chinese Office Action, with English translation, issued in Japanese Patent Application No. CN 2005-80008768.2 dated on May 23, 2008.

(Continued)

*Primary Examiner* — Hung Vu
*Assistant Examiner* — Vernon P Webb
(74) *Attorney, Agent, or Firm* — McDermott Will & Emery LLP

(57) ABSTRACT

A plurality of semiconductor layers including a light-emitting layer (14) are formed on the main surface of a substrate (10) which is composed of a group III-V nitride semiconductor. A first n-type semiconductor layer (12) containing indium is formed between the light-emitting layer (14) and the substrate (10), thereby reducing the affect of damage in the substrate surface. By having such a structure, there is realized a semiconductor light-emitting device having uniform characteristics.

7 Claims, 9 Drawing Sheets

U.S. PATENT DOCUMENTS

| | | | |
|---|---|---|---|
| 2003/0080341 A1* | 5/2003 | Sakano et al. | 257/79 |
| 2003/0132454 A1 | 7/2003 | Lell et al. | |
| 2003/0168653 A1* | 9/2003 | Tsujimura et al. | 257/14 |
| 2003/0205783 A1 | 11/2003 | Ishida | |
| 2004/0041156 A1 | 3/2004 | Tsuda et al. | |
| 2004/0051105 A1* | 3/2004 | Tsuda et al. | 257/79 |
| 2004/0147134 A1* | 7/2004 | Hasegawa et al. | 438/740 |
| 2005/0087753 A1* | 4/2005 | D'Evelyn et al. | 257/98 |
| 2005/0269584 A1* | 12/2005 | Hasegawa et al. | 257/94 |
| 2006/0219998 A1* | 10/2006 | Sato et al. | 257/12 |

FOREIGN PATENT DOCUMENTS

| | | |
|---|---|---|
| JP | 11-214798 A | 8/1999 |
| JP | 11-233893 | 8/1999 |
| JP | 2000-174341 | 6/2000 |
| JP | 2000-174341 A | 6/2000 |
| JP | 2001-60719 A | 3/2001 |
| JP | 2001-168385 | 6/2001 |
| JP | 2001-345476 A | 12/2001 |
| JP | 2002-261014 | 9/2002 |
| JP | 2002-329896 | 11/2002 |
| JP | 2002-329896 A | 11/2002 |
| JP | 2003-31552 | 1/2003 |
| JP | 2003-031552 A | 1/2003 |
| JP | 2003-101160 | 4/2003 |

OTHER PUBLICATIONS

Notice of Reasons for Rejection, with English translation thereof, issued in Japanese Patent Application No. 2004-079873, mailed Dec. 14, 2010.

* cited by examiner

NITRIDE-BASED SEMICONDUCTOR LIGHT-EMITTING DIODE AND ILLUMINATING DEVICE

RELATED APPLICATIONS

This application is the U.S. National Phase under 35 U.S.C. §371 of International Application No. PCT/JP2005/005003, filed on Mar. 18, 2005, which in turn claims the benefit of Japanese Application No. 2004-079873, filed on Mar. 19, 2004, the disclosures of which Applications are incorporated by reference herein.

TECHNICAL FIELD

The present invention relates to semiconductor light-emitting devices and illuminating devices. In particular, the present invention relates to light-emitting devices and illuminating devices made of group III-V nitride semiconductor.

BACKGROUND ART

In recent years, light-emitting devices using group III-V nitride semiconductor typified by gallium nitride (GaN) have been expected as next-generation illumination light sources because they can provide light emission in the short wavelength region. Therefore, active research and development is being conducted on the devices (see, for example, Patent Document 1).

Such light-emitting devices are required to have a decreased operating voltage and an enhanced optical power output. To meet this requirement, the devices have employed, instead of insulating substrates such as sapphire substrates, conductive substrates made of group III-V nitride semiconductor such as GaN. In the case of employing the conductive substrate, current is passed in the substrate. Therefore, the resistances of current paths in the device can be reduced to decrease power consumption and the operating voltage of the device, and concurrently to enhance the static breakdown voltage of the device.

FIG. 16 shows a cross-sectional structure of a conventional light-emitting device. Referring to FIG. 16, an n-type semiconductor layer 102 of GaN, a light-emitting layer 105 of indium gallium nitride (InGaN), and a p-type semiconductor layer 106 of aluminum gallium nitride (AlGaN) are sequentially stacked on a substrate 101 made of n-type GaN. A p-side electrode 107 is formed on the p-type semiconductor layer 106. Respective portions of the p-type semiconductor layer 106, the light-emitting layer 105, and the n-type semiconductor layer 102 are etched to expose a portion of the n-type semiconductor layer 102, and then an n-side electrode 108 is formed on the exposed portion of the n-type semiconductor layer 102 (see, for example, Patent Document 2).

(Patent Document 1) Japanese Unexamined Patent Publication No. 2001-60719
(Patent Document 2) Japanese Unexamined Patent Publication No. 2001-345476

DISCLOSURE OF INVENTION

Problems to be Solved by Invention

When the semiconductor substrate such as GaN is used for the substrate, however, polishing or the like of the surface thereof is needed for planarization. This polishing causes physical damages to the surface of the semiconductor substrate, which in turn disturbs the crystal structure of the semiconductor substrate surface or creates nonuniform strain. In response to this, the semiconductor layers formed over the semiconductor substrate also suffer the disturbance of the crystal structure thereof or nonuniform strain, which results in variations in characteristics of the light-emitting device.

The surface of the semiconductor substrate made of GaN is inclined relative to the (0001) plane of the plane direction of the GaN crystal, but the angle of inclination (off-angle) varies with the location on the substrate. Thus, the properties of each semiconductor layer formed over the substrate differ depending on where the layer is fabricated on the substrate. Furthermore, the variation range of the off-angle differs among the substrates, so that the properties of the semiconductor layer also differ among the substrates. This causes the problem that the characteristics of the individual light-emitting devices, such as optical power output and operating voltage, vary widely and resulting percent defective of the device is raised.

An object of the present invention is to solve the conventional problems described above and to provide a light-emitting device of group III-V nitride semiconductor which is fabricated on a semiconductor substrate, reduces the influence of damages in the substrate and of off-angle variations on the surface substrate, and has uniform characteristics.

Means for Solving the Problems

To attain the above object, the present invention is designed so that in a semiconductor light-emitting device, an n-type semiconductor layer containing In is provided between a substrate and a light-emitting layer.

To be more specific, a semiconductor light-emitting device of the present invention comprises: a substrate made of group III-V nitride semiconductor; a first n-type semiconductor layer containing indium and formed over a main surface of the substrate; and a light-emitting layer formed over the first n-type semiconductor layer.

With the semiconductor light-emitting device of the present invention, the first n-type semiconductor layer containing indium is provided therein. By such a structure, the first n-type semiconductor layer containing indium and being relatively soft can reduce nonuniform strain and abnormal growth resulting from damages in and the off-angle on the substrate surface, so that the occurrence of nonuniform strain can be prevented also in the semiconductor layers including the light-emitting layer formed over the substrate. Therefore, both the in-substrate and substrate-to-substrate properties of the semiconductor layers can be made uniform, which in turn realizes semiconductor light-emitting devices with uniform operating characteristics.

Preferably, in the semiconductor light-emitting device of the present invention, the substrate is made of gallium nitride. By employing the substrate of gallium nitride with an excellent crystallinity, characteristics of the semiconductor light-emitting device can be improved.

Preferably, in the semiconductor light-emitting device of the present invention, the main surface of the substrate is polished, and the main surface of the substrate may be etched. Preferably, the main surface of the substrate is planarized.

Preferably, in the semiconductor light-emitting device of the present invention, the light-emitting layer has a multiple quantum well structure formed by alternately stacking a quantum well layer and a barrier layer, and the quantum well layer has a thickness of 1 to 2.5 nm inclusive. Such a structure can reduce the influence resulting from off-angle variations on the substrate surface and given to the light-emitting layer, so that the characteristics of the respective semiconductor light-emitting devices can certainly be made uniform.

Preferably, in the semiconductor light-emitting device of the present invention, the first n-type semiconductor layer is made of a compound whose general formula is represented by $In_aAl_bGa_{1-a-b}N$ (0<a<1, 0≦b≦1, a+b≦1). By such a structure, the first n-type semiconductor layer can certainly reduce the influence of damages in and off-angle variations on the substrate surface. Preferably, in this case, the aluminum content of the first n-type semiconductor layer is 3% or lower.

Preferably, in the semiconductor light-emitting device of the present invention, the first n-type semiconductor layer has a thickness of 10 nm to 1 μm inclusive. By such a structure, the first n-type semiconductor layer can certainly reduce the influence of damages in and off-angle variations on the substrate surface.

Preferably, the semiconductor light-emitting device of the present invention further comprises a second n-type semiconductor layer formed between the substrate and the first n-type semiconductor layer. By such a structure, the lattice constant matching between the first n-type semiconductor layer and the substrate can be facilitated. Preferably, in this case, the second n-type semiconductor layer is made of a compound whose general formula is represented by $In_cAl_dGa_{1-c-d}N$ (0≦c<1, 0≦d<1, c+d<1).

Preferably, in the semiconductor light-emitting device of the present invention, the second n-type semiconductor layer is an n-type contact layer. Such a structure can reduce the contact resistance with the n-side electrode to decrease the operating voltage of the semiconductor light-emitting device.

Preferably, the semiconductor light-emitting device of the present invention further comprises a third n-type semiconductor layer formed between the first n-type semiconductor layer and the light-emitting layer. Preferably, in this case, the third n-type semiconductor layer is an n-type contact layer. Such a structure can reduce the thicknesses of the second and third n-type semiconductor layers.

Preferably, the semiconductor light-emitting device of the present invention further comprises a fourth n-type semiconductor layer formed between the first n-type semiconductor layer and the light-emitting layer. Such a structure can facilitate uniform current injection into the light-emitting layer. Preferably, in this case, the fourth n-type semiconductor layer is made of a compound whose general formula is represented by $Al_eGa_{1-e}N$ (0≦e<1).

Preferably, in the semiconductor light-emitting device of the present invention, the fourth n-type semiconductor layer is a cladding layer. Preferably, in this case, the cladding layer has a thickness of 5 to 200 nm inclusive.

Preferably, the semiconductor light-emitting device of the present invention further comprises: an n-type contact layer which is formed between the substrate and the light-emitting layer and a portion of which is exposed; an n-side electrode formed on the exposed portion of the n-type contact layer; an n-type cladding layer formed between the first n-type semiconductor layer and the light-emitting layer, a p-type semiconductor layer formed on the light-emitting layer; and a p-side electrode formed over the p-type semiconductor layer, and the device is mounted with an element formation surface thereof facing a submount for mounting. Such a structure can reduce the chip area of the semiconductor light-emitting device.

A illuminating device of the present invention comprises the multiple semiconductor light-emitting devices of the present invention. Such a structure can realize the illuminating device exhibiting no irregular color and operating stably.

Advantageous Effect of the Invention

With the semiconductor light-emitting device of the present invention, a light-emitting device made of group III-V nitride semiconductor can be realized which is formed on a semiconductor substrate, reduces the influence of damages in the substrate and of variations in the angle of inclination on the substrate surface, and has uniform characteristics.

BRIEF DESCRIPTION OF THE DRAWINGS

FIG. 2(a) is a plan view thereof, and FIG. 2(b) is a sectional view thereof taken along the line IIb-IIb.

Figure 1:
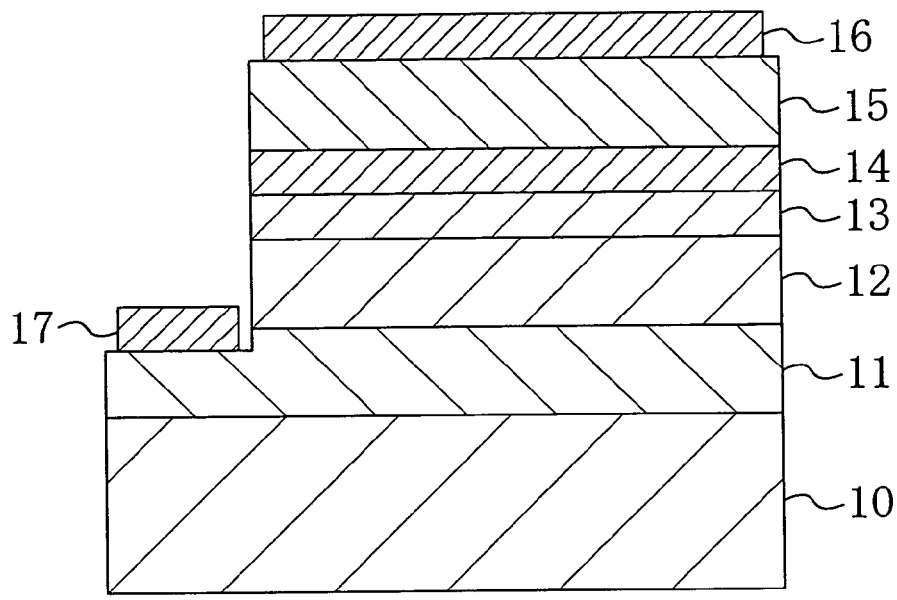
FIG. 1 is a sectional view showing an exemplary light-emitting device according to a first embodiment of the present invention.

EXPLANATION OF REFERENCES 10 substrate
10a (0001) plane
11 n-type contact layer

12 In-containing n-type semiconductor layer
13 n-type cladding layer
14 light-emitting layer
14a quantum well layer
14b barrier layer
15 p-type semiconductor layer
16 p-side electrode
17 n-side electrode
18 translucent electrode
21 n-type cladding layer
31 n-type spacer layer
41 n-type intermediate layer
51 submount
52 p-side substrate electrode
53 n-side substrate electrode
54 bump
55 bump
60 light-emitting unit
61 light-emitting device
62 lead frame
63 wire
64 lead frame
65 molding resin
70 illuminating device
71 feeding terminal
80 main body
81 slot

BEST MODE FOR CARRYING OUT THE INVENTION

First Embodiment

A light-emitting device of group III-V nitride semiconductor and its fabrication method according to a first embodiment of the present invention will be described with reference to the accompanying drawings. FIG. 1 shows a cross-sectional structure of the light-emitting device according to the first embodiment of the present invention.

Referring to FIG. 1, an n-type contact layer 11 is formed on a substrate 10 made of gallium nitride (GaN). On the n-type contact layer 11, an n-type semiconductor layer 12 containing indium (In), an n-type cladding layer 13, a light-emitting layer 14, and a p-type semiconductor layer 15 are sequentially stacked to expose a portion of the top surface of the n-type contact layer 11.

The exposed portion of the n-type contact layer 11 is formed with an n-side electrode 17, and a p-side electrode 16 is formed on the p-type semiconductor layer 15. Note that the n-type contact layer 11 is thinner in the region formed with the n-side electrode 17 than in the other region.

The following description will be made of the principle by which the uniformity of light emitting properties is improved in the light-emitting device of the first embodiment.

The substrate 10 is polished in order to planarize the surface thereof. This causes physical damages to the surface of the substrate 10, and thereby crystal dislocations or the like occur in the surface of the substrate 10. In addition, the surface of the substrate 10 made of GaN is inclined relative to the (0001) plane of the plane direction of the GaN crystal, and the angle of inclination (off-angle) varies with the location on the substrate. If a semiconductor layer is formed on such a substrate 10, nonuniform strain is created in the formed semiconductor layer. This causes variations in light emitting properties within the surface.

Figure 2A:
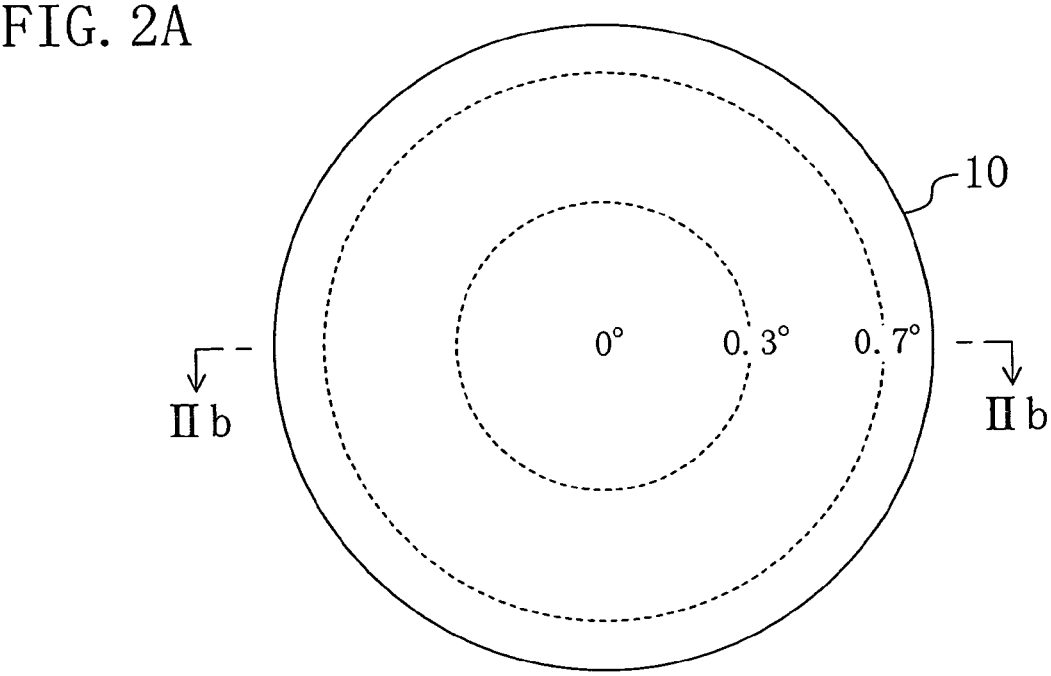
FIGS. 2(a) and 2(b) show the structure of a substrate employed in a light-emitting device according to the first embodiment of the present invention.
Figure 2B:
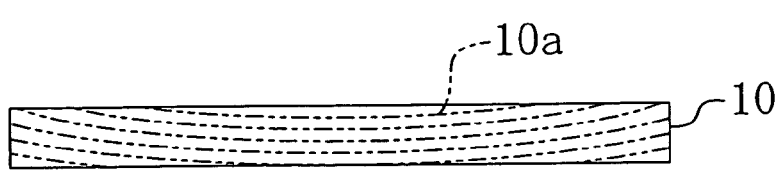

FIGS. 2(a) and 2(b) show an exemplary structure of the substrate 10 made of GaN. FIG. 2(a) shows the plan structure thereof, and FIG. 2(b) shows a cross-sectional structure thereof taken along the line IIb-IIb in FIG. 2(a). As shown in FIG. 2, the top surface of the substrate 10, which is an element formation surface, is inclined relative to the (0001) plane 10a of the plane direction of the GaN crystal, and the angle of inclination (off-angle) is about one degree at a maximum. The direction of inclination is the <11-20> direction, the <10-10> direction, or a direction between the <11-20> direction and the <10$^{-10}$> direction of the crystal. Note that the (0001) plane of the plane direction means the c-plane in the hexagonal system.

The off-angle of the top surface of the substrate 10 increases from the center toward the perimeter. This is because the (0001) plane bows in a concave shape during epitaxial growth of GaN on a substrate made of different type of material, such as sapphire, and the bowing surface is then planarized by polishing.

However, in the light-emitting device of the first embodiment, the n-type semiconductor layer 12 containing In is formed between the light-emitting layer 14 and the substrate 10. Since this n-type semiconductor layer 12 contains In, it becomes softer than the n-type contact layer 11 and the n-type cladding layer 13. Therefore, nonuniform strain caused in the semiconductor layers including the light-emitting layer 14 can be reduced which is generated by damages in the surface of the substrate 10 and variation in the off-angle, and also abnormal growth of the layers can be reduced which is generated likewise. As a result, the light-emitting layer 14 can emit light with a uniform optical power output.

For the In-containing n-type semiconductor layer 12, use can be made of group III-V nitride semiconductor which contains In and whose general formula is represented by $In_aAl_bGa_{1-a-b}N$ ($0<a\leq1$, $0\leq b<1$, $a+b\leq1$). For ease of fabrication, InGaN not containing Al is preferred. The In content a is not particularly limited. However, in order to prevent emitted light from being absorbed in the In-containing n-type semiconductor layer 12, it is preferable to set the content to have a wider band gap than the energy corresponding to the wavelength of the emitted light.

In consideration of the effect of absorbing strain caused by damages in the substrate 10, the In content a is preferably 1% or higher. Moreover, if the In content a is 10% or lower, the thickness of the In-containing n-type semiconductor layer 12 can be reduced. This offers the effect of suppressing the occurrence of crystal defects in the In-containing n-type semiconductor layer 12. In particular, if the In content a of the compound in its entirety is from 2% to 7% inclusive, the effect of absorbing strain or improving the crystallinity becomes remarkable, which is more preferable for the device.

If indium aluminum gallium nitride (InAlGaN) is used for the In-containing n-type semiconductor layer 12, the resulting layer has a smaller lattice constant than the case of using InGaN because it contains aluminum (Al). This prevents the substrate 10 from bowing in a convex shape, which provides an improved flatness of the substrate 10. If light emitted from the light-emitting layer 14 has a wavelength ranging within the ultraviolet region, a preferable use for the In-containing n-type semiconductor layer 12 is made of InAlGaN having a wider band gap and absorbing less light than InGaN. In this case, the Al content b is preferably 3% or less. If the Al content b is 3% or higher, the In-containing n-type semiconductor layer 12 and the semiconductor layer formed on the In-containing n-type semiconductor layer 12 have poor crystallinities.

The In-containing n-type semiconductor layer 12 preferably has a thickness of 10 to 1000 nm inclusive. The In-containing n-type semiconductor layer 12 having a thickness of 10 nm or greater provides the effect of reducing nonuniform strain or abnormal growth resulting from the influence of the off-angle of the substrate 10 and damages in the surface of the substrate 10. Moreover, the In-containing n-type semiconductor layer 12 having a thickness of 1000 nm or smaller can prevent degradation in crystallinity of the In-containing n-type semiconductor layer 12 and also shorten the time for fabrication. In particular, if the In-containing n-type semiconductor layer 12 has a thickness of 20 to 100 nm inclusive, a more significant effect as described above can be exerted, which is further preferable for the device.

It is also acceptable that the In-containing n-type semiconductor layer 12 is a non-doped layer. However, doping with an n-type impurity such as silicon (Si) or germanium (Ge) can enhance current spread across the plane of the layer. In this case, the electron concentration is preferably not less than $1\times10^{17}$ cm$^{-3}$ and less than $1\times10^{20}$ cm$^{-3}$.

For the substrate 10, use can be made of group III-V nitride semiconductor whose general formula is represented by $In_cAl_dGa_{1-c-d}N$ (where $0\leq c\leq 1$, $0\leq d\leq 1$, $c+d\leq 1$). AlGaN which has a c value of zero or contains no In has a good crystallinity, so that it is preferred for the device. Of such semiconductor, GaN which has a d value of zero and which contains no Al is relatively easy to fabricate and can have the best crystallinity, so that it is more preferred for the device. Although the substrate 10 may not be doped, a substrate doped with an n-type impurity such as Si or Ge can provide a decreased element resistance. In doping the substrate, the electron concentration preferably ranges from $1\times10^{17}$ to $1\times10^{20}$ cm$^{-3}$ inclusive. The reason for this is as follows. An electron concentration lower than $1\times10^{17}$ cm$^{-3}$ raises resistivity, which makes it difficult for electrons injected into the substrate 10 to spread in the substrate 10. An electron concentration higher than $1\times10^{20}$ cm$^{-3}$ causes a poor crystallinity of the substrate 10 because of doping with a high concentration of an n-type impurity.

For the n-type contact layer 11, use can be made of n-type group III-V nitride semiconductor having almost the same lattice constant as the substrate 10. By using such a layer, microscopic unevenness can be filled which exists on the substrate 10 of group III-V nitride semiconductor. Moreover, the distance from the substrate 10 to the light-emitting layer 14 can be increased. Therefore, in the case where the surface of the substrate 10 is contaminated by impurities and the like, the effect in which it becomes difficult for the contaminated interface to affect the light-emitting layer 14 can be provided. Furthermore, group III-V nitride semiconductor having almost the same lattice constant as the substrate 10 is grown on the substrate 10, whereby the n-type contact layer 11 can be formed without creating new strain. Therefore, the In-containing n-type semiconductor layer 12 to be grown on the n-type contact layer 11 can be formed with stability. If the In-containing n-type semiconductor layer 12 is thickened in order to increase the distance from the substrate 10 to the light-emitting layer 14, cracks tend to occur in the In-containing n-type semiconductor layer 12. On the other hand, even though the n-type contact layer 11 having almost the same lattice constant as the substrate 10 is grown thick, cracks are difficult to cause therein.

For the n-type contact layer 11, use can be made of a compound whose general formula is represented by $In_eAl_fGa_{1-e-f}N$ ($0\leq e<1$, $0\leq f<1$, $e+f<1$). Even in the case of InGaN or InAlGaN containing In, if the In content e is low, the resulting compound has a lattice constant approximating to the lattice constant of the substrate 10. Therefore, it can be used for the n-type contact layer 11. In addition, the layer may be made of not only a single-layer film but also a stack film.

The n-type contact layer 11 is preferably doped with an n-type impurity such as Si or Ge, and its electron concentration is preferably not less than $1\times10^{17}$ cm$^{-3}$ and less than $1\times10^{20}$ cm$^{-3}$. The reason for this is as follows. An electron concentration lower than $1\times10^{17}$ cm$^{-3}$ raises the ohmic contact resistance with the n-side electrode 17 to increase the operating voltage of the light-emitting device. An electron concentration of $1\times10^{20}$ cm$^{-3}$ or higher causes a poor crystallinity of the n-type contact layer 11 because of doping with a high concentration of an n-type impurity. If the n-type contact layer 11 is made of a stacked film, it is sufficient that at least a film in contact with the n-side electrode 17 is doped.

The thickness of the n-type contact layer 11 is desirably 100 nm or greater. The reason for this is as follows: the n-type contact layer 11 thinner than 100 nm requires a very high etching accuracy in forming, on the n-type contact layer 11, an exposed surface for formation of the n-side electrode 17, which makes it difficult to form the exposed surface. The thickness of the n-type contact layer 11 has no specific upper limit. However, in order to shorten the formation time of the n-type contact layer 11 and improve the production efficiency of the device, the thickness is preferably set at 5 μm or smaller.

For the n-type cladding layer 13, use can be made of a compound whose general formula is represented by $Al_gGa_{1-g}N$ ($0\leq g<1$). By employing the n-type cladding layer 13 made of group III-V nitride semiconductor with a wider band gap than the In-containing n-type semiconductor layer 12, hole overflow from the light-emitting layer 14 can be effectively prevented. Although the n-type cladding layer 13 is preferably doped with an n-type impurity, it may be doped with no n-type impurity. If it is doped with an n-type impurity, it is recommended that the carrier concentration of the cladding layer 13 is lower than those of the n-type contact layer 11 and the In-containing n-type semiconductor layer 12. By employing such a structure, the n-type cladding layer 13 has a higher resistance than the n-type contact layer 11, so that the n-type cladding layer 13 blocks electron flow from the n-type contact layer 11 through the n-type cladding layer 13 toward the light-emitting layer 14. Thus, electrons spread uniformly at the interface between the In-containing n-type semiconductor layer 12 and the n-type cladding layer 13. Therefore, uniform electron injection into the light-emitting layer 14 can be realized to uniformize spatial distribution of light emission from the light-emitting layer 14. As a result of this, a uniform plane emission of light can be provided from the back surface of the substrate 10 serving as the main light-emitting plane.

The n-type cladding layer 13 preferably has a thickness of 5 to 200 nm inclusive. The reason for this is as follows. The n-type cladding layer 13 having a thickness smaller than 5 nm weakens the effect of preventing hole overflow, while the layer having a thickness greater than 200 nm raises the series resistance of the light-emitting device to increase the operating voltage.

For the light-emitting layer 14, use can be made of group III-V nitride semiconductor having a narrower band gap than the n-type contact layer 11 and the p-type semiconductor layer 15. In particular, InGaN or GaN containing no Al can be used to enhance the emission intensity of light with a wavelength ranging from ultra-violet to green visible region. In the case where the light-emitting layer 14 contains In, the layer 14 formed into a single quantum well layer with a thickness smaller than 10 nm can improve the crystallinity of the light-emitting layer 14 to enhance the light emission efficiency to a further extent.

The light-emitting layer 14 may be composed of a multiple quantum well structure made by alternately stacking a quantum well layer of InGaN or GaN and a barrier layer of InGaN, GaN, or AlGaN having a wider band gap than the quantum well layer. If emission of light with a short wavelength is required, InAlGaN may be used for the quantum well layer.

For the p-type semiconductor layer 15, use can be made of p-type group III-V nitride semiconductor having a wider band gap than the light-emitting layer 14. By using such a layer, the function as a p-type cladding layer can be imparted to the p-type semiconductor layer 15. For the p-type semiconductor layer 15, use can be made of a single layer film or a stacked film of a compound (or compounds) represented by $In_hAl_iGa_{1-h-i}N$ ($0 \leq h<1$, $0 \leq i<1$, $h+i<1$). In particular, by using AlGaN containing Al and not containing In for at least a layer coming into contact with the light-emitting layer 14, electrons can be confined efficiently in the light-emitting layer 14 to enhance the light emission efficiency.

For a p-type impurity to be doped in the p-type semiconductor layer 15, use can be made of magnesium (Mg), zinc (Zn), cadmium (Cd), carbon (C) or the like. For ease of handling, use of Mg is preferred. The concentration of the p-type impurity is preferably $1 \times 10^{19}$ to $5 \times 10^{20}$ cm$^{-3}$ inclusive. The reason for this is as follows. A p-type impurity concentration lower than $1 \times 10^{19}$ cm$^{-3}$ raises the ohmic contact resistance with the p-side electrode 16 to increase the operating voltage of the light-emitting device. A p-type impurity concentration higher than $5 \times 10^{20}$ cm$^{-3}$ causes a poor crystallinity of the p-type semiconductor layer 15 because of doping with a high concentration of a p-type impurity, and induces significant diffusion of the p-type impurity into the light-emitting layer 14 to degrade the light emission efficiency.

The p-type semiconductor layer 15 preferably has a thickness of 50 to 500 nm inclusive. The reason for this is as follows. The layer with a thickness smaller than 50 nm causes metal forming the p-side electrode 16 to enter the light-emitting layer 14 due to electromigration or the like, which reduces the life of the light-emitting device. The layer with a thickness greater than 500 nm raises voltage drop occurring when holes pass through the p-type semiconductor layer 15, which increases the operating voltage of the light-emitting device.

If the p-type semiconductor layer 15 is composed of a stacked film, a film coming into contact with the p-side electrode 16 can be made of GaN or InGaN with a relatively narrow band gap. This reduces the contact resistance between the p-side electrode 16 and the p-type semiconductor layer 15 to effectively decrease the operating voltage.

In doping the p-type semiconductor layer 15 with a relatively high concentration of p-type impurity, an intermediate layer is preferably introduced between the light-emitting layer 14 and the p-type semiconductor layer 15 in order to suppress an excess diffusion of the p-type impurity into the light-emitting layer 14. For this intermediate layer, use can be made of group III-V nitride semiconductor such as InAlGaN. In the case of using GaN or AlGaN, the crystallinity of the interface with the light-emitting layer 14 can be maintained satisfactorily. In order for the intermediate layer to serve as a layer for absorbing the p-type impurity diffusing in the direction of the light-emitting layer 14, an undoped intermediate layer is preferred. The intermediate layer preferably has a thickness of 1 to 50 nm inclusive. The layer having a thickness smaller than 1 nm weakens the effect of preventing diffusion of the p-type impurity into the light-emitting layer 14, while the layer having a thickness greater than 50 nm reduces the efficiency of hole injection into the light-emitting layer 14 to decrease the light emission efficiency.

For the p-side electrode 16, use can be made of a single metal film, an alloy film, or a stacked film composed of one or more substances of gold (Au), nickel (Ni), platinum (Pt), palladium (Pd), magnesium (Mg), and the like. In particular, if use is made of metal having a high reflectivity at a wavelength of emitted light, such as silver (Ag), platinum (Pt), magnesium (Mg), aluminum (Al), zinc (Zn), rhodium (Rh), ruthenium (Ru), palladium (Pd), or the like, light traveling from the light-emitting layer 14 toward the p-side electrode 16 can be reflected and taken out of the backside of the substrate 10. This enables enhancement of the light emission intensity.

The n-side electrode 17 is formed on the exposed portion of the n-type contact layer 11 having exposed by removing portions of the In-containing n-type semiconductor layer 12, the n-type cladding layer 13, the light-emitting layer 14, and the p-type semiconductor layer 15. By arranging the n-side electrode 17 in this manner, the back surface of the substrate 10 can serve as a main light-emitting surface, and the main light emitting surface can provide uniform surface light emission.

For the n-side electrode 17, use can be made of a single metal film composed of aluminum (Al), titanium (Ti), or the like. Alternatively, an alloy film or a stacked film containing one or more of aluminum (Al), titanium (Ti), gold (Au), nickel (Ni), vanadium (V), chromium (Cr), or the like may be used therefor.

A p-type cladding layer may be formed between the light-emitting layer 14 and the p-type semiconductor layer 15. Preferably, the p-type cladding layer is formed of group III-V nitride semiconductor with a wider band gap than the light-emitting layer 14, and particularly formed of a component which is doped with a p-type impurity such as Mg and whose general formula is represented by $Al_jGa_{1-j}N$ ($0 \leq j<1$). In most cases, in order to form the p-type cladding layer with a good crystallinity, formation of the p-type cladding layer is conducted at a growth temperature higher than the suitable temperature for the growth of the light-emitting layer 14. Thus, after growth of the light-emitting layer 14 and then during elevation of chamber temperature to the growth temperature of the p-type cladding layer, constituent elements of the light-emitting layer 14, such as indium and nitrogen, may dissociate or the like to degrade the crystallinity of the light-emitting layer 14. To avoid such a trouble, after formation of the light-emitting layer 14, a portion of the p-type cladding layer is successively grown during temperature elevation, and when the chamber temperature reaches a suitable temperature for the growth of the p-type cladding layer, the remaining portion of the p-type cladding layer is successively grown. Thereby, degradation of crystallinity of the light-emitting layer 14 can be prevented effectively. In this procedure, a portion of the p-type cladding layer to be grown during temperature elevation preferably has a composition whose general formula is represented by $Al_kGa_{1-k}N$ ($0 \leq k<1$, $k \leq 5$). This is because by forming the layer to come into contact with the light-emitting layer 14, it can exert a sufficient function as a p-type cladding layer and concurrently it can enhance the effect of preventing degradation of crystallinity of the light-emitting layer 14 due to dissociation or the like of constituting element.

Figure 3:
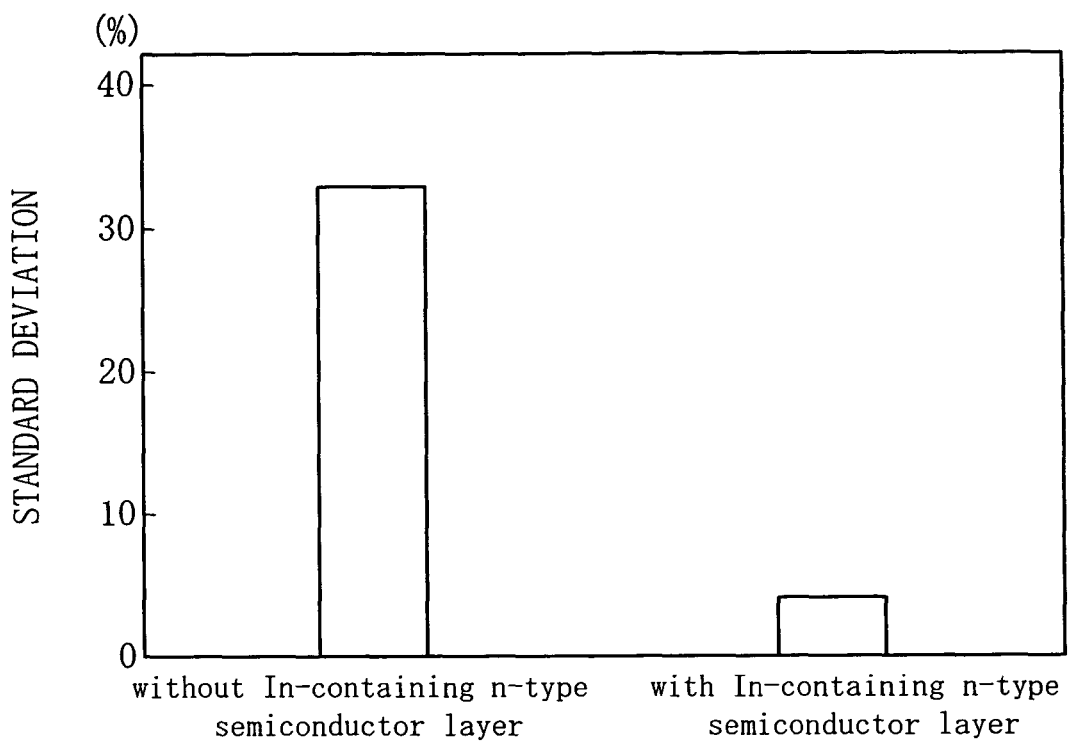
FIG. 3 is a graph showing the distributions of photoluminescence intensity obtained by a substrate formed with a semiconductor layer employed in the light-emitting device of the first embodiment of the present invention and by a substrate of a conventional example for comparison.

Hereinafter, characteristics of the light-emitting device according to the first embodiment will be described with reference to the accompanying drawings. FIG. 3 shows the distribution of photoluminescence intensity obtained by a stacked film made of group III-V nitride semiconductor, containing the light-emitting layer 14, and formed on the substrate 10. The photoluminescence intensity was measured at a pitch of 1 mm by a photoluminescence mapping system using a He—Cd laser beam with a wavelength of 325 nm as an excitation light source. Note that the substrate used for this measurement has a diameter of 50 mm.

As shown in FIG. 3, for the conventional stacked film of group III-V nitride semiconductor not provided with the In-containing n-type semiconductor layer 12, the standard deviation of photoluminescence intensity was 32.9%, which indicates very wide variations. On the other hand, for the stacked film of the present invention made of group III-V nitride semiconductor and provided with the In-containing n-type semiconductor layer 12, the standard deviation was 4.1%, from which it is obvious that the light-emitting layer 14 is formed uniformly on the substrate.

Further, when the light-emitting device of the first embodiment was driven by a forward current of 20 mA, it was able to emit blue light with a peak emission wavelength of about 470 nm and perform a uniform surface light emission from the back surface of the substrate 10. The optical power output obtained at this time varied little among individual light emitting diodes, and its value was about 6 mW, which was substantially stable. Also, the forward operating voltage was about 3.0 V, which was substantially stable. On the other hand, in the case of not providing the In-containing n-type semiconductor layer 12, the optical power output varies within the range of 3 to 6 mW, and the operating voltage also varies within the range of 3.0 to 3.3 V.

As described above, the light-emitting device according to the first embodiment of the present invention has the In-containing n-type semiconductor layer 12 provided between the substrate 10 and the light-emitting layer 14. By such a structure, irregular strain resulting from damages caused by polishing the substrate 10 or from variations in the off-angle on the substrate surface can be prevented from being created in the semiconductor layers formed on the substrate 10, and also abnormal growth resulting from those phenomena can be prevented from occurring in the semiconductor layers. This results in a reduced variation in characteristics of a plurality of light-emitting devices fabricated on the substrate 10. Furthermore, the light-emitting devices fabricated on a plurality of substrates 10, respectively, can have uniform characteristics.

Note that the surface of the substrate 10 may be etched by a reactive ion etching method. The etched substrate has fewer damages than the substrate subjected to polishing only.

For example, the substrate 10 was polished to have a flat, mirror-finished surface, and then the GaN substrate 10 was placed within a reactive ion etching apparatus. While chlorine gas serving as a process gas was flowed at a flow rate of 10 mL/min (1013 hPa, 0° C.) and the high-frequency power and the substrate temperature were set at 100 W and 50° C., respectively, the surface of the GaN substrate 10 was etched by a thickness of about 100 nm. Subsequently, the n-type contact layer 11, the In-containing n-type semiconductor layer 12, the n-type cladding layer 13, the light-emitting layer 14, and the p-type semiconductor layer 15 were sequentially stacked on the etched substrate 10, and then the in-plane distribution of the photoluminescence intensity over the wafer were measured. From this measurement, the standard deviation of photoluminescence intensity over the substrate having a diameter of 50 mm was 3.0%.

Variations in photoluminescence intensity were narrower for the substrate subjected to etching after polishing than for the substrate subjected to polishing only. This is because etching can reduce damages in the substrate surface.

Further, electrodes were formed on the stacked structure of semiconductor layers formed in the above manner. After packaging thereof, the optical power output and the operating voltage were measured. When the fabricated device was driven by a forward current of 20 mA, it was able to emit blue light with a peak emission wavelength of about 470 nm and perform a uniform surface light emission. The optical power output obtained at this time varied little among individual light emitting diodes, and its value was about 6 mW, which was substantially stable. Also, the forward operating voltage was about 3.0 V, which was substantially stable.

First Modification of First Embodiment

Figure 4:
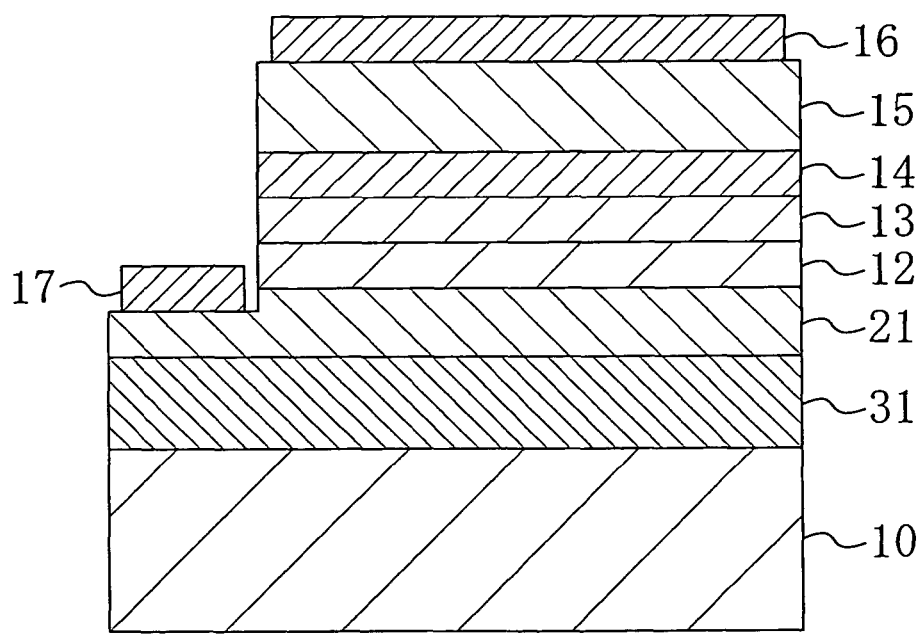
FIG. 4 is a sectional view showing a light-emitting device according to a first modification of the first embodiment of the present invention.

A light-emitting device according to a first modification of the first embodiment of the present invention will be described below with reference to the accompanying drawings. FIG. 4 shows a cross-sectional structure of the light-emitting device according to the first modification. The description of the components shown in FIG. 4 that are the same as those shown in FIG. 1 will be omitted by retaining the same reference numerals.

Referring to FIG. 4, in the light-emitting device of the first modification, an n-type spacer layer 31 with a lower carrier concentration than an n-type contact layer 21 is provided between the n-type contact layer 21 and the substrate 10. For the n-type spacer layer 31, use can be made of a compound whose general formula is represented by $In_eAl_fGa_{1-e-f}N$ ($0 \leq e < 1$, $0 \leq f < 1$, $e+f < 1$) like the n-type contact layer 21.

Thus, by employing the structure made by stacking the n-type spacer layer 31 with a lower carrier concentration and the n-type contact layer 21 with a higher carrier concentration, the n-type contact layer 21 in contact with the n-side electrode 17 can be thinned to increase the carrier concentration. In order to improve the crystallinity of the top surface of the n-type contact layer 21, the n-type contact layer 21 must have a certain thickness. However, if the n-type contact layer 21 with a high carrier concentration is thickened, crack tends to be created therein.

However, in the first modification, the n-type spacer layer 31 having a lower carrier concentration and resisting creation of cracks is provided between the n-type contact layer 21 and the substrate 10. Therefore, even though the n-type contact layer 21 is thinned, the crystallinity of the top surface of the n-type contact layer 21 can be improved. Moreover, a space can be provided between the light-emitting layer 14 and the substrate 10, which prevents the pollution of the light-emitting layer by impurities on the surface of the substrate 10.

Preferably, in this case, the carrier concentration of the n-type spacer layer 31 is not less than $1 \times 10^{17}$ cm$^{-3}$ and less than $2 \times 10^{18}$ cm$^{-3}$. The reason for this is as follows. The n-type spacer layer 31 having a carrier concentration less than $1 \times 10^{17}$ cm$^{-3}$ raises the series resistance of the n-type spacer layer 31 to increase the operating voltage of the element, while the layer having a carrier concentration of $2 \times 10^{18}$ cm$^{-3}$ or more easily causes cracks therein.

Preferably, the carrier concentration of the n-type contact layer 21 is not less than $2 \times 10^{18}$ cm$^{-3}$ and less than $1 \times 10^{19}$ cm$^{-3}$. The reason for this is as follows. The n-type contact layer 21 having a carrier concentration less than $2 \times 10^{18}$ cm$^{-3}$ makes it difficult to sufficiently reduce the contact resistance with the n-side electrode 17. The n-type contact layer 21 having a carrier concentration of $1 \times 10^{19}$ cm$^{-3}$ or more has a degraded crystallinity, which in turn degrades the crystallinity of the light-emitting layer 14 or other layers formed over the n-type contact layer 21 to reduce the optical power output.

Preferably, the n-type contact layer 21 is made thinner than the n-type spacer layer 31, and has a thickness of 100 to 500 nm inclusive. The n-type contact layer 21 having a thickness smaller than 100 nm makes it difficult to control etching for exposing the surface of the n-type contact layer 21. The n-type contact layer 21 having a thickness greater than 500 nm has a degraded crystallinity, which in turn degrades the crystallinity of the light-emitting layer 14 or other layers formed over the n-type contact layer 21 to reduce the optical power output.

The thickness of the n-type spacer layer 31 is preferably 1 to 5 μm inclusive. The reason for this is as follows. The n-type spacer layer 31 having a thickness smaller than 1 μm tends to raise the series resistance of the element to increase the operating voltage. The layer having a thickness greater than 5 μm tends to cause cracks.

Second Modification of First Embodiment

Figure 5:
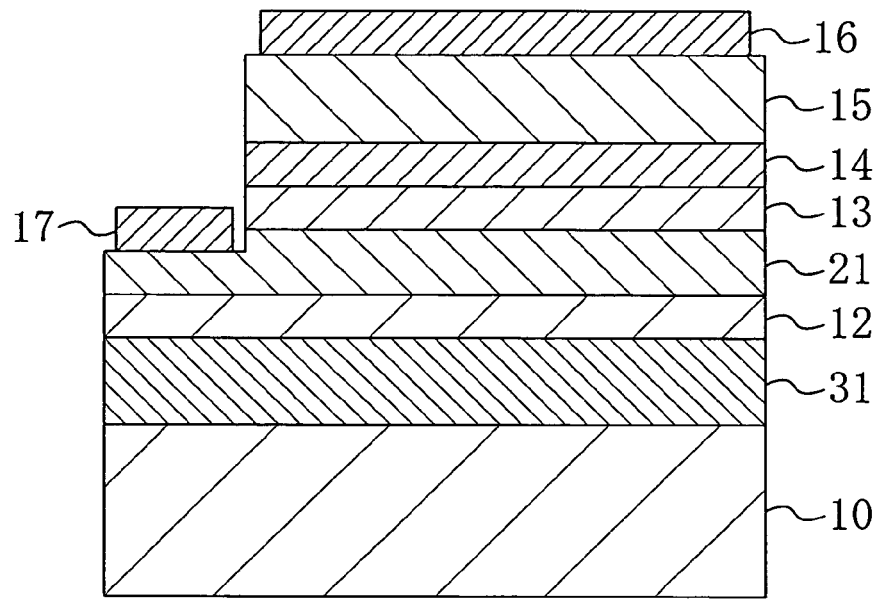
FIG. 5 is a sectional view showing a light-emitting device according to a second modification of the first embodiment of the present invention.

A light-emitting device according to a second modification of the first embodiment of the present invention will be described below with reference to the accompanying drawings. FIG. 5 shows a cross-sectional structure of the light-emitting device according to the second modification. The description of the components shown in FIG. 5 that are the same as those shown in FIG. 1 will be omitted by retaining the same reference numerals.

Referring to FIG. 5, in the light-emitting device of the second modification, the In-containing n-type semiconductor layer 12 is provided between the n-type contact layer 21 and the n-type spacer layer 31. Even in the case where the n-type contact layer 21 is thus provided above the In-containing n-type semiconductor layer 12, the In-containing n-type semiconductor layer 12 can reduce the influence of damages in the substrate 10.

If the In-containing n-type semiconductor layer 12 is not provided between the n-type spacer layer 31 and the n-type contact layer 21, the total thickness of the n-type spacer layer 31 and the n-type contact layer 21 should be 2 μm or greater in order to obtain the crystallinity of the top surface of the n-type contact layer 21. However, like the second modification, the In-containing n-type semiconductor layer 12 can be provided between the n-type spacer layer 31 and the n-type contact layer 21 to maintain the crystallinity of the top surface of the n-type contact layer 21 even in the case where the total thickness of the n-type spacer layer 31 and the n-type contact layer 21 is set at 2 μM or smaller. However, too small a total thickness will degrade the crystallinities of the n-type cladding layer 13 and the light-emitting layer 14 formed on the n-type contact layer 21, so that the total thickness thereof is preferably 1 μm or greater. As described above, by decreasing the thicknesses of the n-type spacer layer 31 and the n-type contact layer 21, formation thereof can be facilitated and the formation time thereof can be shortened.

The ratio between the thicknesses of the n-type spacer layer 31 and the n-type contact layer 21 is not particularly limited, but the structure in which the n-type contact layer 21 is thicker than the n-type spacer layer 31 can be fabricated more easily.

If the n-type contact layer 21 has a sufficient thickness, the device may be designed so that the n-type spacer layer 31 is not provided and the In-containing n-type semiconductor layer 12 is provided directly on the substrate 10.

Second Embodiment

Figure 6:
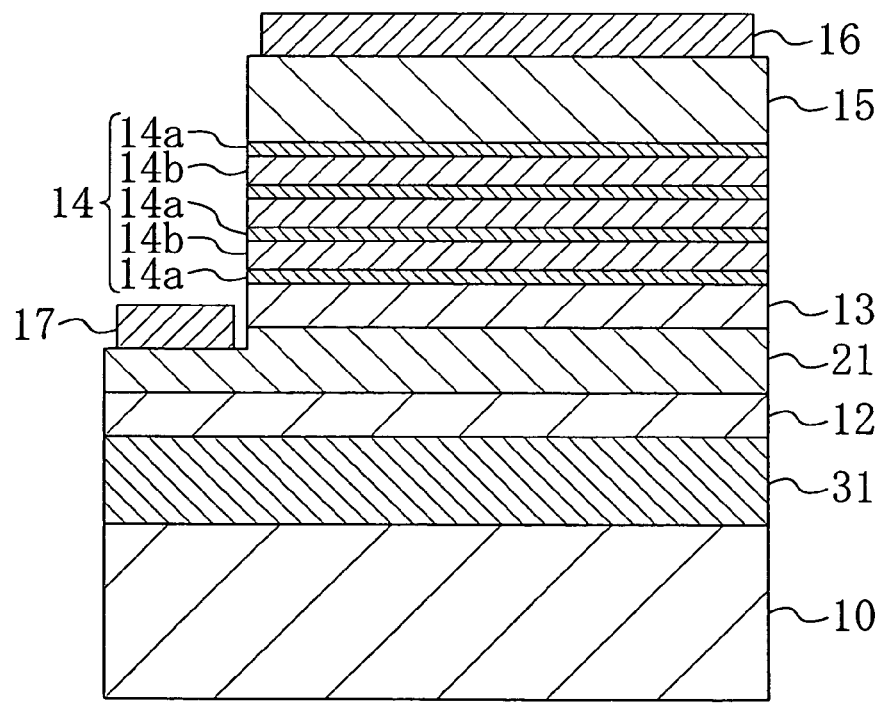
FIG. 6 is a sectional view showing a light-emitting device according to a second embodiment of the present invention.

A light-emitting device of group III-V nitride semiconductor and its fabrication method according to a second embodiment of the present invention will be described with reference to the accompanying drawings. FIG. 6 shows a cross-sectional structure of the light-emitting device according to the second embodiment of the present invention. The description of the components shown in FIG. 6 that are the same as those shown in FIG. 5 will be omitted by retaining the same reference numerals.

Referring to FIG. 6, the light-emitting device of the second embodiment has the light-emitting layer 14 formed as a quantum well structure made by alternately stacking a quantum well layer 14a of InGaN and a barrier layer 14b of GaN. The quantum well layer 14a may be made of GaN or the like instead of InGaN. It is sufficient that the barrier layer 14b is made of a semiconductor layer having a wider band gap than the well layer 14a, and AlGaN, InGaN, InAlGaN, or the like may be used instead of GaN. By such a structure, a light-emitting device covering a wide range of wavelength from about 370 nm to about 660 nm can be realized.

Even in such a case where the light-emitting layer 14 has a quantum well structure, provision of the In-containing n-type semiconductor layer 12 can reduce the influence of damages in the surface of the substrate 10 to decrease variations in characteristics of the light-emitting device fabricated on the semiconductor substrate 10.

Figure 7A:
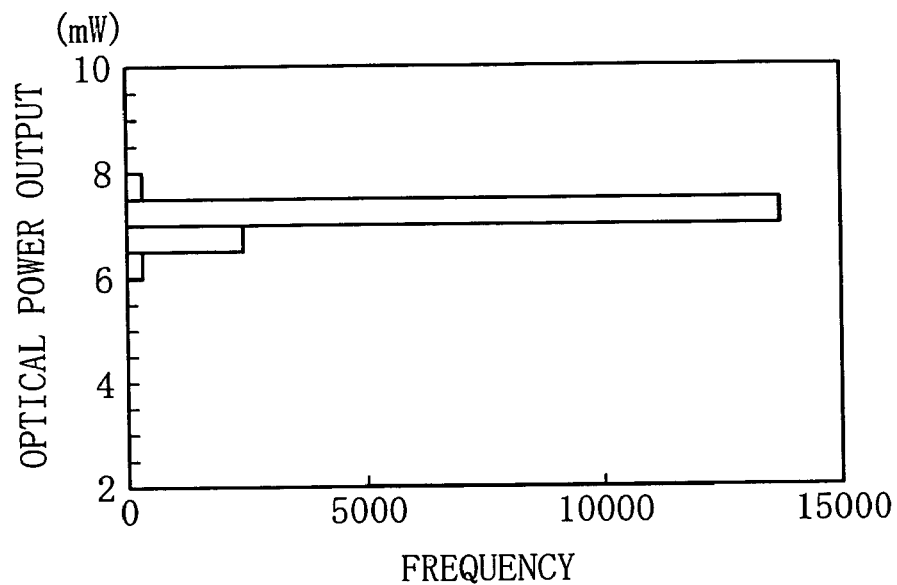
FIGS. 7(a) and 7(b) are graphs showing comparison in distribution of optical power output between the light-emitting device according to the second embodiment of the present invention and the light-emitting device according to the conventional example.
Figure 7B:
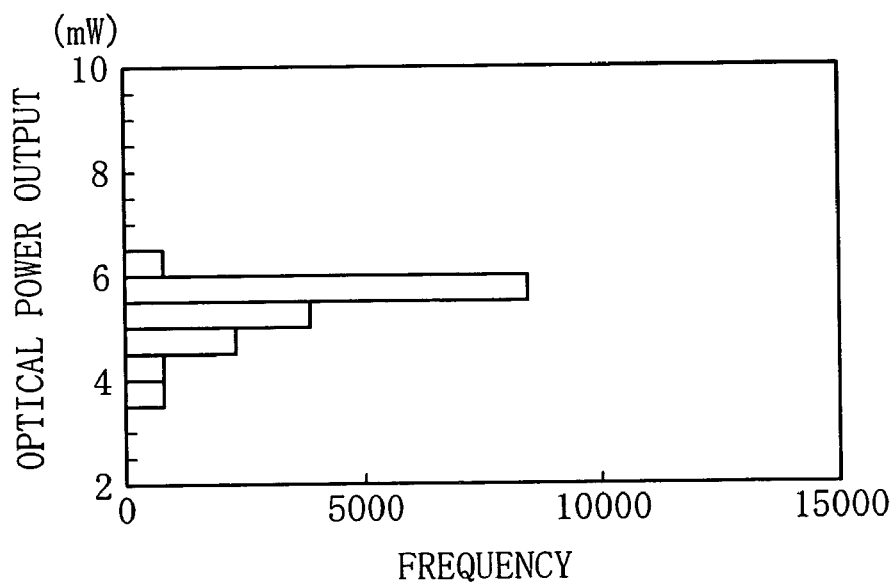

FIGS. 7(a) and 7(b) show distributions of the optical power outputs of the light-emitting devices in the cases where the In-containing n-type semiconductor layer 12 is and is not provided, respectively. Note that the quantum well layer 14a of the light-emitting device used for measurements has a thickness of 1.5 nm.

In the measurements, about 19000 chips were used which were fabricated by splitting the substrate 10 with a diameter of 50 mm into quadrate parts with 320 μm-long sides. The chips put on a transparent adhesive film were placed on an XY stage of an automatic probe test system. Then, probe needles were sequentially put onto the p-side electrode 16 and the n-side electrode 17 of each chip, and passed a current of 20 mA between the two electrodes for 0.01 second, thereby sequentially measuring the optical power output of each chip. The optical power output was obtained so that a light-receiving element placed below the adhesive film received emitted light and the intensity of the received light was multiplied by a certain constant to convert the intensity into the optical output by an integrating sphere. About 2000 light-emitting devices located in a region extending 1 mm inwardly from the perimeter of the substrate 10 were left out of the group of chips to be measured.

As shown in FIG. 7(a), in the case of providing the In-containing n-type semiconductor layer 12, the average optical power output of the light-emitting device was 7.3 mW, and its standard deviation is 0.4 mW, which indicates almost no variations. On the other hand, as shown in FIG. 7(b), in the case of not providing the In-containing n-type semiconductor layer 12, the average optical power output of the light-emitting device was 5.8 mW and its standard deviation is 1.2 mW. As a result, the optical power output decreased and variations widened as compared to the case of providing the In-containing n-type semiconductor layer 12. From this, it is obvious that the In-containing n-type semiconductor layer 12 can be provided to decrease variations in optical power output.

In the case where the light-emitting layer is composed of a quantum well structure, the quantum well layer 14a preferably has a thickness of 1 nm or greater. This is because the quantum well layer 14a with a thickness of 1 nm or smaller greatly reduces the optical power output.

Figure 8:
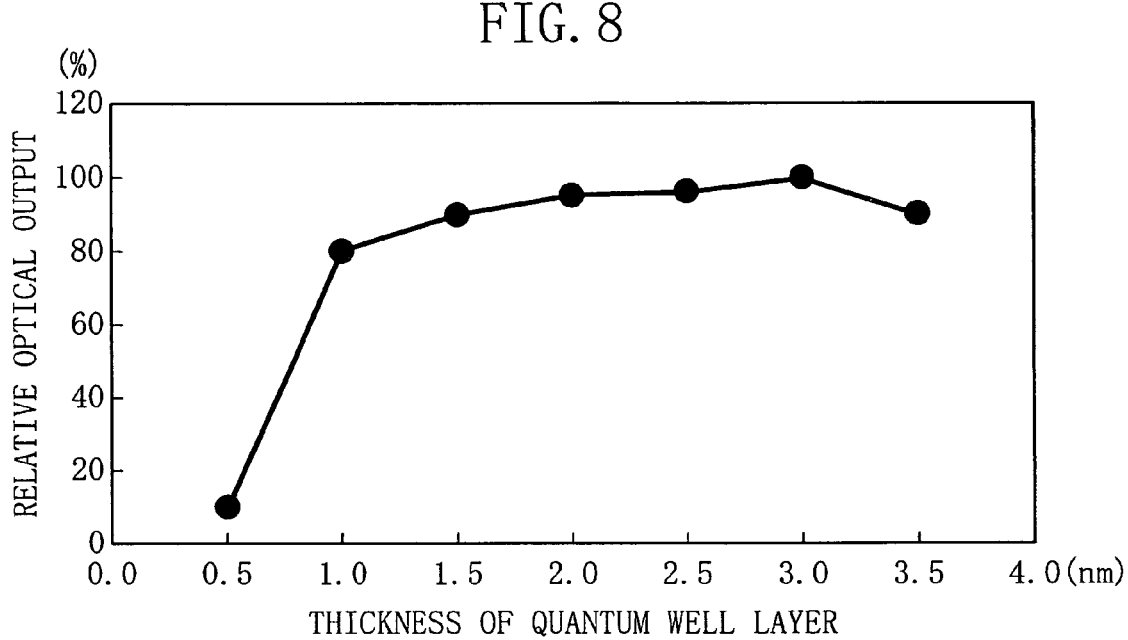
FIG. 8 is a graph showing the correlation between the thickness of a quantum well layer and the optical power output of the light-emitting device according to the second embodiment of the present invention.

FIG. 8 shows the relation between the thickness of the quantum well layer 14a of the light-emitting device and the optical power output of the light-emitting device. Referring to FIG. 8, the quantum well layer 14a with a thickness of 1.0 nm or smaller provides a sharply reduced optical power output.

This is probably because thinning of the quantum well layer 14a causes an easy carrier overflow.

Furthermore, the quantum well layer 14a preferably has a thickness of 2.5 nm or smaller. This is because the quantum well layer 14a with a great thickness causes variations in characteristics of the light-emitting device due to variations in the off-angle on the substrate surface.

Figure 9:
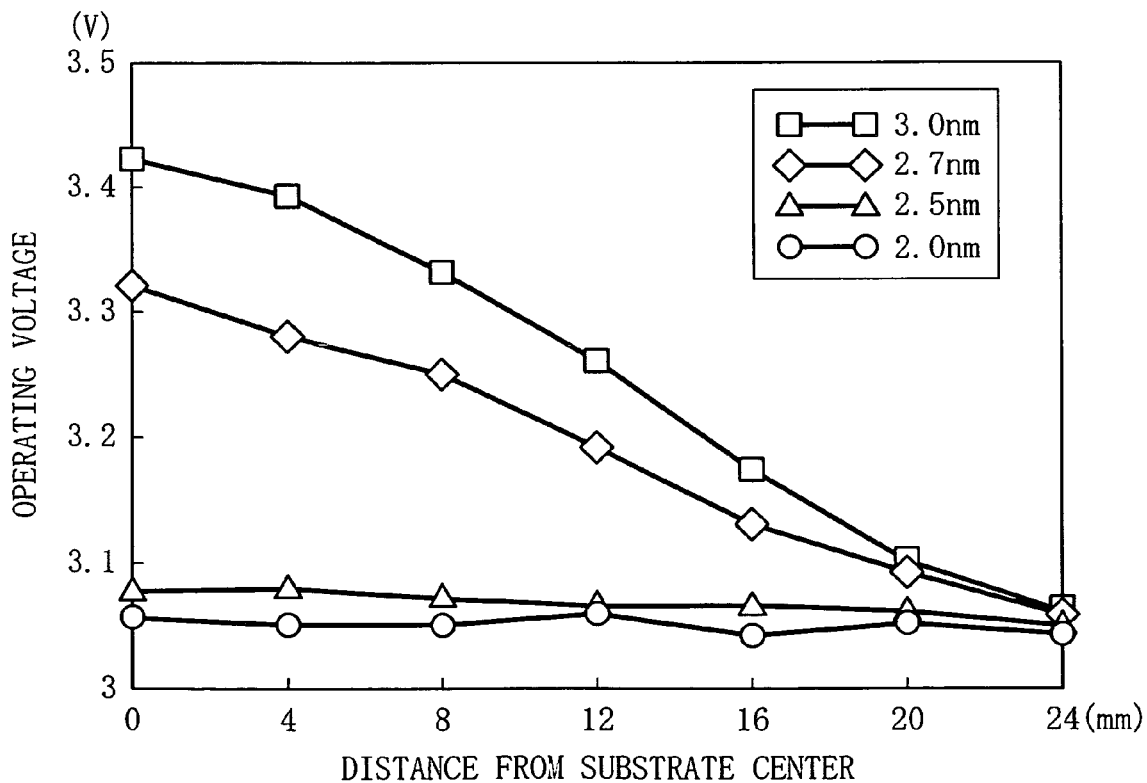
FIG. 9 is a graph showing the correlations between the formation position on a substrate and the operating voltage of the light-emitting device according to the second embodiment of the present invention.

FIG. 9 shows the correlations between the position of the light-emitting device formed on the substrate 10 and the operating voltage, which are obtained based on the quantum well layers 14a having different thicknesses. In FIG. 9, the ordinate represents the operating voltage of the light-emitting device, while the abscissa represents the formation position of the light-emitting device as the distance from the center of the substrate 10.

When the thickness of the quantum well layer 14a is 2.5 nm or smaller, the light-emitting device formed at any position on the substrate 10 has a low operating voltage and variations in operating voltage are not recognized. However, when the thickness of the quantum well layer 14a is 2.7 nm or greater, the light-emitting device formed at a closer position to the center of the substrate has a higher operating voltage.

This is probably because the electrical resistivity of the quantum well layer 14a made of InGaN depends on the off-angle of the surface of the substrate 10 and the thickness of the quantum well layer 14a. The quantum well layer 14a made of InGaN is grown in an atmosphere containing no hydrogen at a lower temperature than the growth temperature of the cladding layer made of GaN. Thus, migration is relatively unlikely to occur on the surface of the grown film. Therefore, around the center of the substrate 10 where the off-angle of the crystal plane is nearly zero, a reduced number of steps are present on the surface, which tends to induce three-dimensional island growth. In particular, for the quantum well layer 14a with a great thickness, this trend is considered to become pronounced.

On the other hand, in the perimeter portion of the substrate where the off-angle is relatively large, the density of the step on the surface becomes high. This easily brings two-dimensional step-flow growth. Thus, it is conceivable that when the quantum well layer 14a has a great thickness, the electrical resistivity of the quantum well layer 14a is high around the center of the substrate 10 where the off-angle is small, and the electrical resistivity of the quantum well layer 14a is low around the perimeter portion of the substrate 10 where the off-angle is relatively large.

Figure 10A:
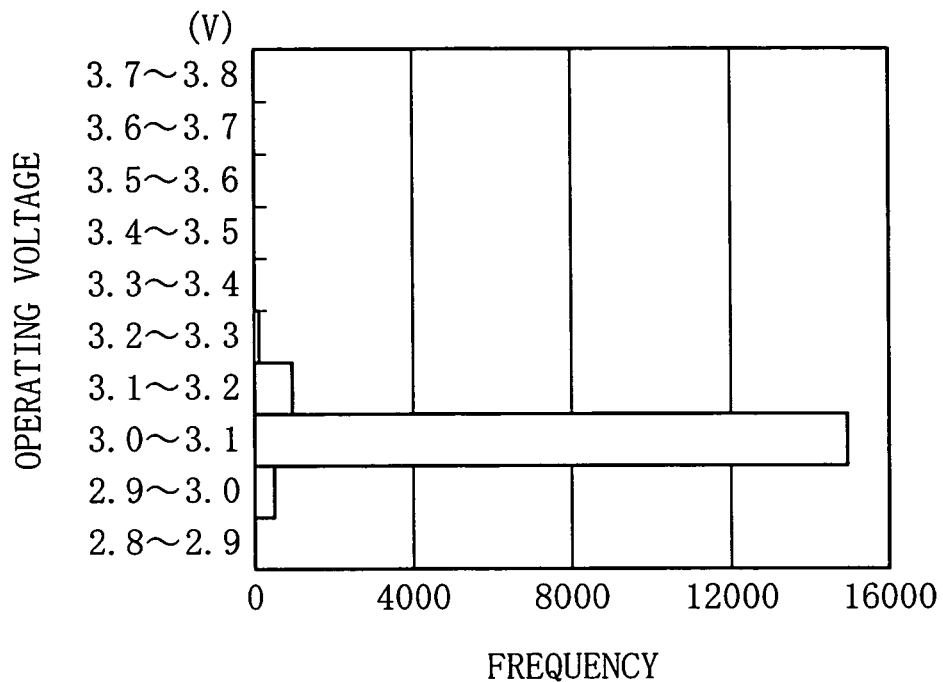
FIGS. 10(a) and 10(b) are graphs showing comparison in distribution of operating voltage between the light-emitting device of the second embodiment of the present invention and the light-emitting device of the conventional example.
Figure 10B:
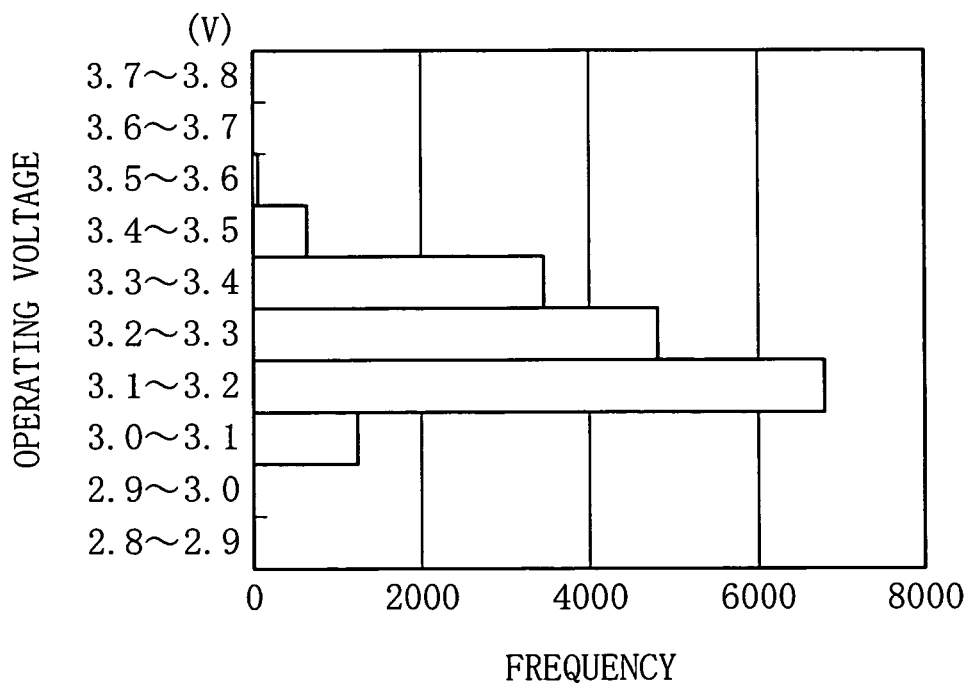

FIGS. 10(a) and 10(b) show distributions of the operating voltages in the cases where a voltage is applied to the light-emitting device having a 1.5 nm-thick quantum well layer 14a and to the device having a 3.0 nm-thick quantum well layer 14a, respectively. Using an automatic probe test system, about 19000 chips were measured which were fabricated by splitting the substrate 10 with a diameter of 50 mm into quadrate parts with 320 μm-long sides. About 2000 light-emitting device located in a region extending 1 mm inwardly from the perimeter of the substrate 10 were left out of the group of chips to be measured.

As shown in FIG. 10(a), in the case where the thickness of the quantum well layer 14a is set at 1.5 nm, the average of the operating voltage of the light-emitting device is 3.05 V, and its standard deviation is 0.01 V, which indicates a very narrow distribution of operating voltage. On the other hand, as shown in FIG. 10(b), in the case where the thickness of the quantum well layer 14a is set at 3.0 nm, the average of the operating voltage is 3.18 V, and its standard deviation is 0.12 V. This indicates that the operating voltage rises and its variation widens as compared with the quantum well layer 14a having a thickness of 1.5 nm.

As described above, the light-emitting device according to the second embodiment of the present invention has the In-containing n-type semiconductor layer 12 provided between the substrate 10 and the light-emitting layer 14. By such a structure, variations in characteristics of the light-emitting device can be reduced which result from irregular strain created in the semiconductor layers on the substrate 10 under the influence of damages caused by polishing the substrate 10 or of variations of the off-angle. Moreover, since the thickness of the quantum well layer 14a is thinned, characteristics of the light-emitting device such as optical power output and operating voltage can be certainly prevented from varying due to variations in the off-angle on the surface of the substrate 10. Therefore, a plurality of light-emitting devices fabricated on one substrate can have uniform characteristics. Furthermore, the light-emitting devices fabricated on a plurality of substrates, respectively, can also have uniform characteristics.

The following description will be made of a fabrication method of the light-emitting device according to the second embodiment.

First, by a vapor-phase growth method using halide, a single crystal film of GaN is grown on the surface of a sapphire substrate to have a thickness of about 370 μm. Thereafter, light of a yttrium aluminum garnet (YAG) laser having a wavelength of 355 nm is applied from the back surface of the sapphire substrate to exfoliate the single crystal film from the sapphire substrate.

Next, the GaN single crystal film is attached onto a holding disc with the exfoliated surface facing below, and using a polishing system, the surface of the film is polished with abrasive grains containing fine diamond particles to have a flat, mirror-finished surface. Then, the GaN single crystal film is removed from the disc and cleaned with organic solvent and acid solution. In this manner, the GaN single crystal film is formed into the substrate 10 which is made of GaN and has a thickness of about 350 μm and a diameter of about 50 mm.

Subsequently, the substrate 10 is placed on a substrate holder within a reaction tube. While the temperature of the substrate 10 is kept at 1060° C. for ten minutes, the substrate 10 is heated with hydrogen gas, nitrogen gas, and ammonia flowed thereon, thereby removing contamination of organic or other substances and moisture adhering onto the surface of the substrate 10, and concurrently improving the crystallinity of the substrate 10.

Then, with nitrogen gas and hydrogen gas flowed as main carrier gas, ammonia, trimethyl gallium (TMG), and monosilane are supplied to grow the n-type spacer layer 31 made of Si-doped GaN and having a thickness of 400 nm.

After growth of the n-type spacer layer 31, the temperature of the substrate 10 is dropped to 750° C. In the state in which this temperature is kept, ammonia, TMG, trimethyl indium (TMI), trimethyl aluminum (TMA), and monosilane are supplied with nitrogen gas flowed as main carrier gas, thereby growing the In-containing n-type semiconductor layer 12 made of Si-doped InAlGaN and having a thickness of 50 nm.

The substrate 10 is then heated to 1060° C., and ammonia, TMG, and monosilane are supplied with nitrogen gas and hydrogen gas flowed as main carrier gas, thereby growing the n-type contact layer 21 made of Si-doped GaN and having a thickness of 600 nm.

After growth of the n-type contact layer 21, the temperature of the substrate 10 is kept at 1060° C. In this state, ammonia, TMG, and TMA are supplied with nitrogen gas and hydrogen gas flowed as main carrier gas, thereby growing the n-type cladding layer 13 made of undoped AlGaN and having a thickness of 20 nm.

After growth of the n-type cladding layer 13, the temperature of the substrate 10 is dropped to 700° C. With nitrogen gas flowed as main carrier gas, ammonia, TMG, and TMI are supplied to grow the quantum well layer 14a of a quantum well structure which is made of undoped InGaN and has a thickness of 1.5 nm. After growth of the quantum well layer 14a, supply of TMI is stopped and ammonia and TMG are supplied to form the barrier layer 14b made of undoped GaN and having a thickness of 10 nm. By repeatedly conducting the same procedure a desired number of times, the light-emitting layer 14 is formed which is composed of four cycles of quantum well layers 14a and three cycles of barrier layers 14b.

After growth of the light-emitting layer 14, ammonia, TMG, and TMA are supplied with nitrogen gas flowed as main carrier gas, and simultaneously the temperature of the substrate 10 is elevated toward 1000° C. After the temperature of the substrate 10 reaches 1000° C., ammonia, TMG, TMA, and bis(cyclopentadienyl) magnesium ($Cp_2Mg$) are supplied with nitrogen gas and hydrogen gas flowed as main carrier gas, thereby growing the p-type semiconductor layer 15 made of Mg-doped AlGaN and having a thickness of 200 nm.

After growth of the p-type semiconductor layer 15, supply of TMG, TMA, and $Cp_2Mg$ is stopped. With nitrogen gas and ammonia flowed, the substrate 10 is cooled to about room temperature, and then the substrate 10 with a stacked film of group III-V nitride semiconductor formed on the surface thereof is taken out from the reaction tube.

On the stacked film of group III-V nitride semiconductor formed in the above manner, a $SiO_2$ film is deposited by a CVD method. Then, by photolithography and reactive ion etching, a mask of $SiO_2$ is formed which exposes part of the surface of the p-type semiconductor layer 15.

Subsequently, by a reactive ion etching method, portions of the p-type semiconductor layer 15, the light-emitting layer 14, the n-type cladding layer 13 are removed to expose the surface of the n-type contact layer 21.

After removal of the $SiO_2$ etching mask by wet etching, by photolithography and evaporation, the p-side electrode 16 having a thickness of about 1 μm is formed by evaporation on almost the entire surface of the p-type semiconductor layer 15. The p-side electrode 16 is made by sequentially stacking Pt, Rh, Ti, and Au in this order. Then, by photolithography and evaporation, Ti and Au are sequentially stacked on part of the top surface of the exposed n-type contact layer 11 to form by evaporation the n-side electrode 17 with a thickness of about 600 nm.

The resulting substrate 10 is attached onto a disc of ceramic with the back surface thereof facing outward, and then the substrate 10 is ground and polished to adjust the thickness thereof to 100 μm.

After the substrate 10 is removed from the disc, a third-order harmonic of a YAG laser with a wavelength of 355 nm is applied from the front surface side of the substrate 10 to form a V-shaped groove in the substrate 10. The groove has a width of 10 μm and a depth of 40 μm. The resulting substrate 10 is placed on a transparent adhesive film, and a cutter is put from the back surface side of the substrate 10 in accordance with the V-shaped groove position, and then pressed against the V-shaped groove. Thereby, the substrate is split into quadrate chips each having sides of 320 μm and a thickness of 100 μm.

Figure 11:
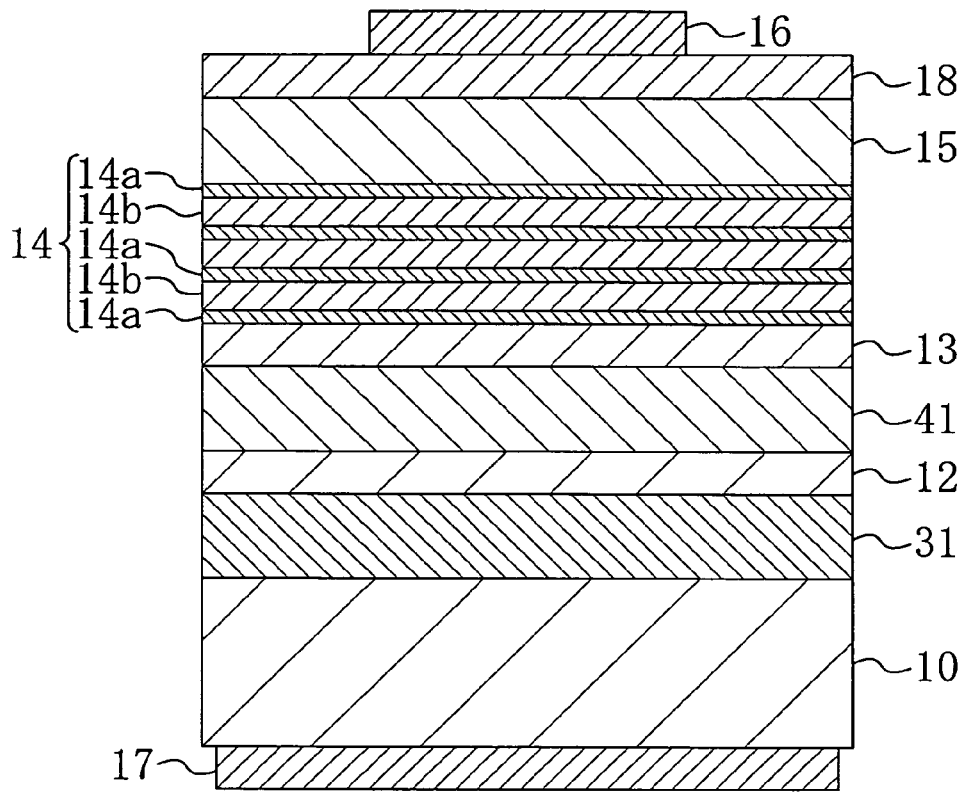
FIG. 11 is a sectional view showing a light-emitting device according to one modification of the second embodiment of the present invention.

Note that in the second embodiment, the n-type contact layer is formed above the buffer semiconductor layer like the second modification of the first embodiment. Alternatively, as shown in the first embodiment and the first modification thereof, it may be formed below the buffer semiconductor layer Modification of Second Embodiment A light-emitting device according to one modification of the second embodiment of the present invention will be described below with reference to the accompanying drawings. FIG. 11 shows a cross-sectional structure of the light-emitting device according to this modification. The description of the components shown in FIG. 11 that are the same as those shown in FIG. 6 will be omitted by retaining the same reference numerals.

Referring to FIG. 11, the light-emitting device of this modification has the n-side electrode 17 provided on the back surface of the substrate 10. By such a structure, provided between the In-containing n-type semiconductor layer 12 and the n-type cladding layer 13 is an n-type intermediate layer 41 instead of the n-type contact layer 21.

Further, a translucent electrode 18 is provided on the top surface of the p-type semiconductor layer 15, and emitted light is taken from the semiconductor layer formation surface thereof. Provision of the translucent electrode 18 can reduce the area of the p-side electrode 16, so that light absorption by the p-side electrode 16 can be avoided. Moreover, since the area of the translucent electrode 18 can be increased, a current can be passed uniformly through the light-emitting layer 14. This enhances the optical power output and reduces the operating voltage. It is sufficient that the translucent electrode 18 is formed of a known indium tin oxide (ITO) film or the like.

Furthermore, by providing the n-side electrode 17 on the back surface of the substrate 10, the necessity to perform etching for exposing the surface of the n-type contact layer is eliminated, which enables simplification of fabrication steps. Note that for the n-type intermediate layer 41, use can be made of a semiconductor layer having the same composition as the n-type contact layer 21 in the second embodiment.

In the case where emitted light is taken from the back surface of the substrate 10, the n-side electrode 17 may be provided not on the back surface of the substrate 10 but on the front surface of the substrate 10 exposed by removing respective portions of the n-type spacer layer 31, the In-containing n-type semiconductor layer 12, the n-type intermediate layer 41, the n-type cladding layer 13, the light-emitting layer 14, and the p-type semiconductor layer 15. In this case, the electron concentration of the substrate 10 is set equal to or higher than that of the n-type spacer layer 31. By providing the n-side electrode 17 on the front surface of the substrate 10 with a high electron concentration, the ohmic contact resistance of the n-side electrode 17 can be reduced to decrease the operating voltage.

Also, the n-side electrode 17 may be formed on the surface of the In-containing n-type semiconductor layer 12 exposed by removing respective portions of the n-type intermediate layer 41, the n-type cladding layer 13, the light-emitting layer 14, and the p-type semiconductor layer 15. By forming the n-side electrode 17 on the surface of the In-containing n-type semiconductor layer 12 with a narrow band gap, the ohmic contact resistance of the n-side electrode 17 can be reduced.

In this modification, description has been made of the example in which the n-type electrode of the light-emitting device shown in the second embodiment is provided on the back surface of the substrate. In a like manner, the n-type electrode of the light-emitting device shown in the first embodiment or its modifications may be provided on the back surface of the substrate.

Third Embodiment

Figure 12:
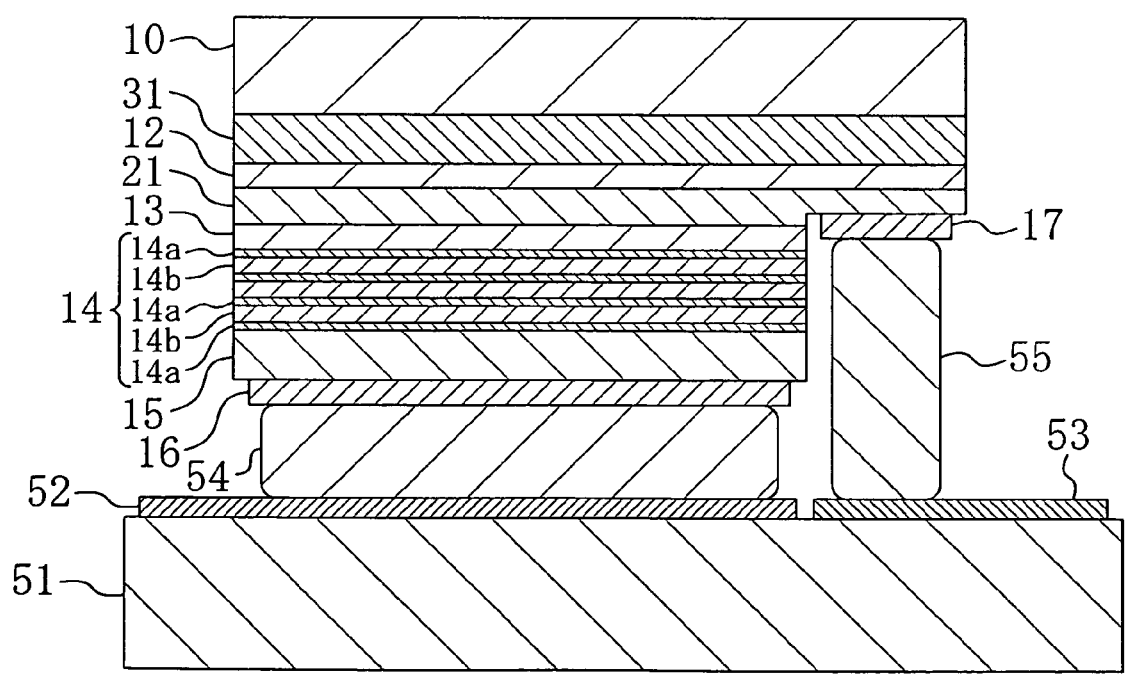
FIG. 12 is a sectional view showing a light-emitting device according to a third embodiment of the present invention.

A light-emitting device according to a third embodiment of the present invention will be described below with reference to the accompanying drawings. FIG. 12 shows a cross-sectional structure of the light-emitting device according to the third embodiment. The description of the components shown in FIG. 12 that are the same as those shown in FIG. 6 will be omitted by retaining the same reference numerals.

Referring to FIG. 12, in the light-emitting device of the third embodiment, the light-emitting device of the second embodiment is flip chip bonded onto a submount 51 with an element formation surface thereof facing below. A p-side substrate electrode 52 and an n-side substrate electrode 53 are provided on the top surface of the submount 51. The p-side substrate electrode 52 and the p-side electrode 16 of the light-emitting device are electrically connected to each other with a bump 54 interposed therebetween, and the n-side substrate electrode 53 and the n-side electrode 17 are electrically connected to each other with a bump 55 interposed therebetween.

When the submount 51 is formed of a zener diode, the static breakdown voltage can be enhanced. In stead of the zener diode, a light-emitting diode, a Si diode, a ceramic, or the like can also be used therefor.

The p-side and n-side substrate electrodes 52 and 53 are formed of a single metal film, an alloy film, or a stacked film composed of Au, Ni, Pt, Pd, Mg, or the like. In particular, by using metal having a high reflectivity at a wavelength of emitted light, such as Ag, Pt, Mg, Al, Zn, Rh, Ru, Pd, or the like, emitted light can be effectively taken out upward.

The following description will be made of a fabrication method of the light-emitting device according to the third embodiment. First, the bumps 54 and 55 made of Au are allowed to adhere to the p-side substrate electrode 52 and the n-side substrate electrode 53 provided on the surface of the submount 51, respectively. Adhesion of the bumps may be conducted by a known ultrasonic bonding method or the like.

Next, while the component formation surface the light-emitting device fabricated by the same procedure as the first embodiment faces downward, the device is allowed to adhere to the submount 51 with the bumps 54 and 55 adhered thereonto. In this adhesion, electrical connection is made between the bump 54 and the p-side electrode 16 and between the bump 55 and the n-side electrode 17. It is sufficient that adhesion of the bump 54 to the p-side electrode 16 and of the bump 55 to the n-side electrode 17 can be made by a known ultrasonic bonding method or the like.

Fourth Embodiment

Figure 13:
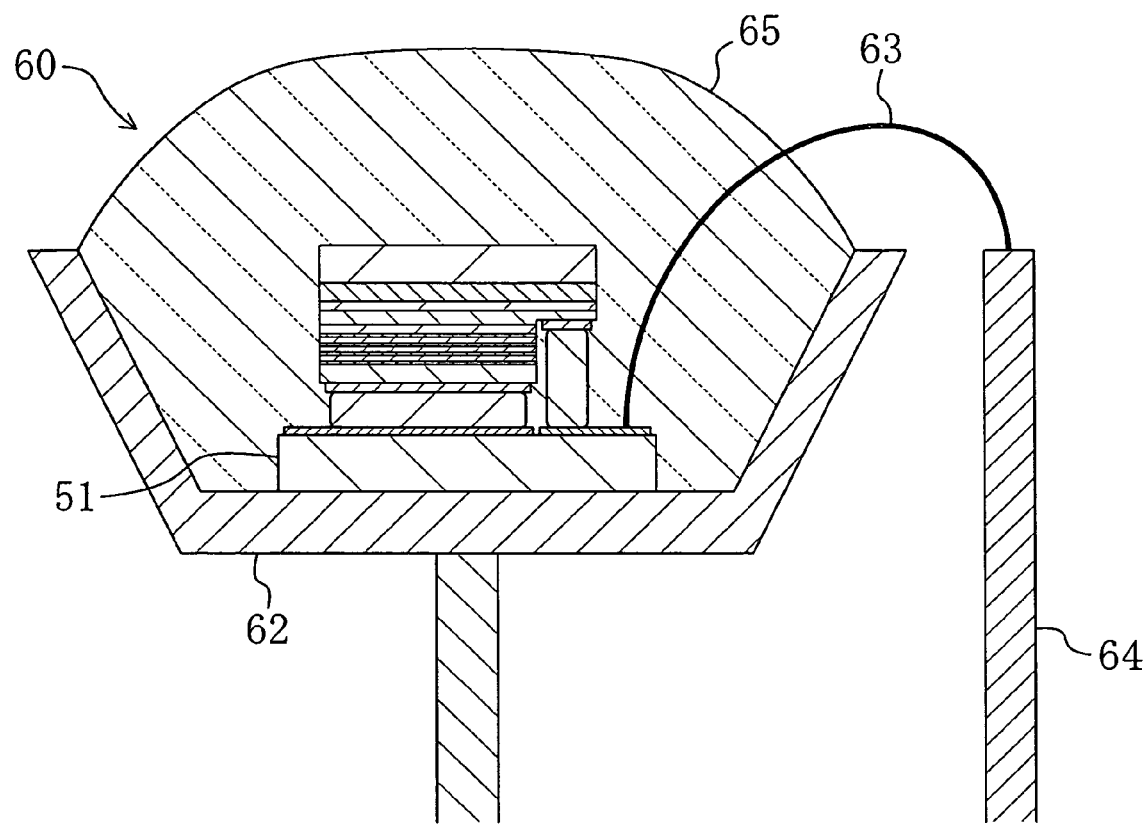
FIG. 13 is a sectional view showing a light-emitting unit employed in an illuminating device according to a fourth embodiment of the present invention.

An illuminating device according to a fourth embodiment of the present invention will be described below with reference to the accompanying drawings. FIG. 13 shows a cross-sectional structure of a light-emitting unit 60 used for the illuminating device according to the fourth embodiment. Referring to FIG. 13, the submount 51 with the light-emitting device adhering thereto is allowed to adhere to the inside of a cup of a lead frame 62 in electrically connected relation with Ag paste or the like. The n-side substrate electrode of the submount 51 is electrically connected to a lead frame 64 with a wire 63 interposed therebetween. The cup of the lead frame 62 is molded with resin 65.

Figure 14:
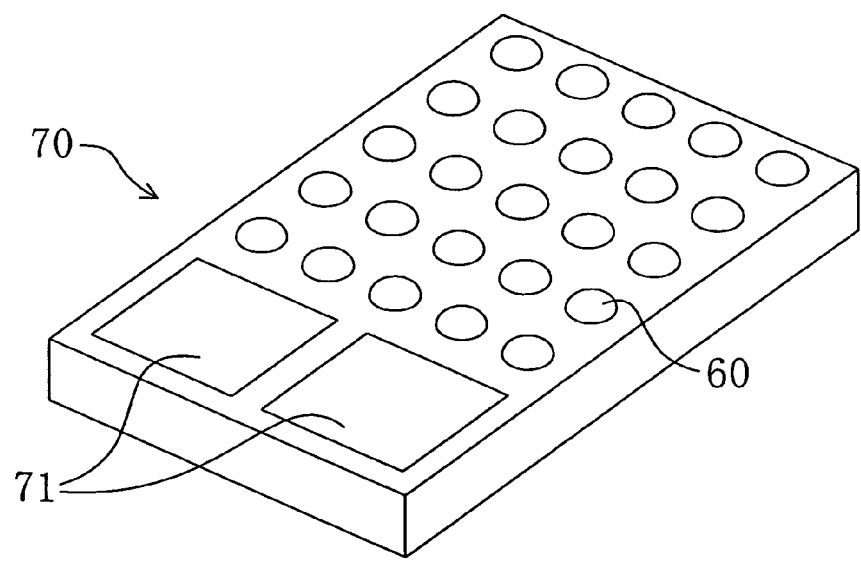
FIG. 14 is a perspective view showing the illuminating device according to the fourth embodiment of the present invention.

FIG. 14 shows the structure of a card-type illuminating device 70 employing a plurality of light-emitting units 60. The surface of the illuminating device 70 is provided with a feeding terminal 71 electrically connected to a wiring pattern and supplying power to the light-emitting units 60.

Figure 15:
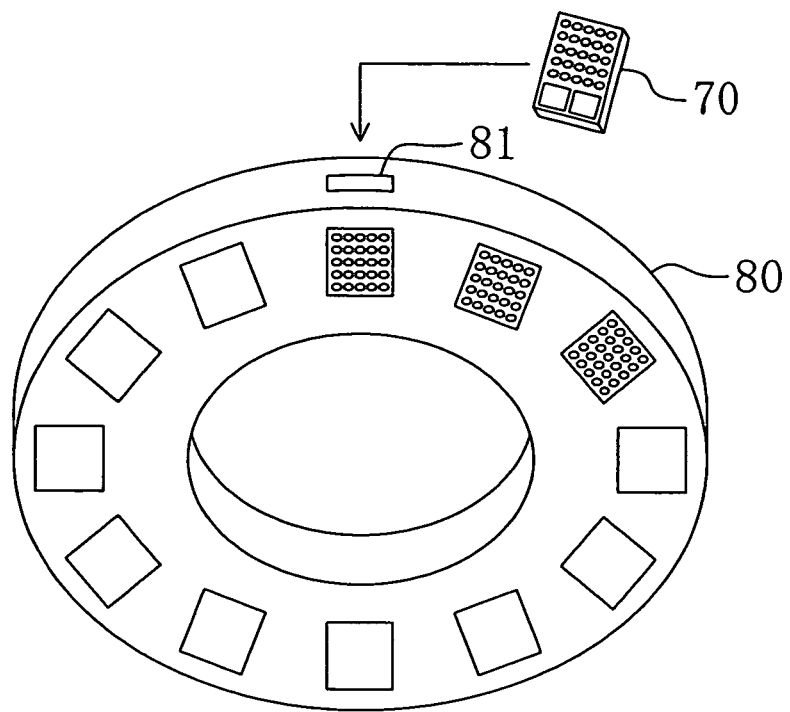
FIG. 15 is a perspective view showing the illuminating device according to the fourth embodiment of the present invention.
Figure 16:
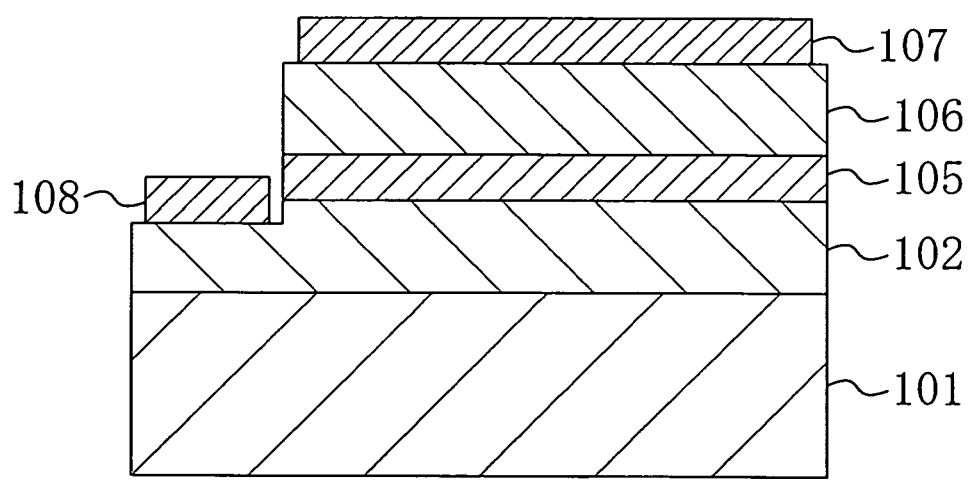
FIG. 16 is a sectional view showing a light-emitting device according to the conventional example.

FIG. 15 shows an exemplary structure of an illuminating device which employs the card-type illuminating devices 70 and is interchangeable with a ring fluorescent lamp. As shown in FIG. 15, the card-type illuminating devices 70 are set within slots 81 provided in a main body 80, respectively, and thus become ready to be lit. The main body 80 has a commercial power source connected thereto and also contains lighting circuitry.

The illuminating device according to the present invention includes the light-emitting units employing the light-emitting devices of the present invention. Therefore, the optical power outputs of the individual light-emitting units are uniform, so that the occurrence of irregular color can be suppressed. Moreover, since the operating voltages of the light-emitting units are also uniform, driving circuitry operates stably to improve the reliability.

Industrial Applicability

The semiconductor light-emitting device and the illuminating device according to the present invention have the advantage that they can realize the light-emitting device of group III-V nitride semiconductor formed on the semiconductor substrate, reducing the influence of damages in the substrate and of variations in the angle of inclination on the substrate surface, and having uniform characteristics. Accordingly, they are useful for semiconductor light-emitting devices, illuminating devices, or the like.

What is claimed is:

1. A light-emitting diode comprising:
    a substrate made of group III-V nitride semiconductor;
    a first n-type semiconductor layer containing indium and formed over a main surface of the substrate;
    a light-emitting layer formed over the first n-type semiconductor layer;
    a second n-type semiconductor layer formed between the substrate and the first n-type semiconductor layer;
    a third n-type semiconductor layer formed between the first n-type semiconductor layer and the light-emitting layer; and
    a fourth n-type semiconductor layer formed between the first n-type semiconductor layer and the light-emitting layer, the fourth n-type semiconductor layer being directly formed on the third n-type semiconductor layer,
    wherein the third n-type semiconductor layer is a contact layer on which an n-side electrode is formed.

2. The diode of claim 1,
    wherein the fourth n-type semiconductor layer is made of a compound whose general formula is represented by $Al_eGa_{1-e}N$ ($0 \leq e < 1$).

3. The diode of claim 2,
    wherein the fourth n-type semiconductor layer is a cladding layer.

4. The diode of claim 3,
    wherein the cladding layer has a thickness of 5 to 200 nm inclusive.

5. An illuminating device comprising multiple light-emitting diodes,
    wherein the diodes including:
    a substrate made of group III-V nitride semiconductor;
    a first n-type semiconductor layer containing indium and formed over a main surface of the substrate;

a light-emitting layer formed over the first n-type semiconductor layer;

a second n-type semiconductor layer formed between the substrate and the first n-type semiconductor layer;

a third n-type semiconductor layer formed between the first n-type semiconductor layer and the light-emitting layer; and a fourth n-type semiconductor layer formed between the first n-type semiconductor layer and the light-emitting layer, the fourth n-type semiconductor layer being directly formed on the third n-type semiconductor layer, wherein the third n-the semiconductor layer is a contact layer on which an n-side electrode is formed.

6. The diode of claim 1, wherein the first n-type layer is a monolayer.

7. The illuminating device of claim 5, wherein the first n-type layer is a monolayer.

\* \* \* \* \*